United States Patent [19]
Ferzli

[11] Patent Number: 6,050,960
[45] Date of Patent: Apr. 18, 2000

[54] LAPAROSCOPIC INSTRUMENT

[76] Inventor: George S. Ferzli, 48 Merrick Ave., Staten Island, N.Y. 10301

[21] Appl. No.: 09/082,275

[22] Filed: May 20, 1998

[51] Int. Cl.⁷ ..................................................... A61B 5/103
[52] U.S. Cl. ............................................. 600/587; 33/773
[58] Field of Search .................................... 600/587, 593; 235/95 R, 95 B; D10/70; 33/772, 773, 779, 782

[56] References Cited

U.S. PATENT DOCUMENTS

| | | | |
|---|---|---|---|
| 5,560,119 | 10/1996 | LeBreton | 33/773 |
| 5,780,846 | 7/1998 | Angilella et al. | 33/773 |

*Primary Examiner*—Michael Buiz
*Assistant Examiner*—Julian W. Woo
*Attorney, Agent, or Firm*—Jordan and Hamburg LLP

[57] ABSTRACT

A laparoscopic instrument which permits distance measurements to be taken internal of a body includes a wheel rotatably mounted at a distal end of an elongated barrel portion. The wheel is placed in contact with an internal body part to be measured and rotation is imparted to the wheel, either by self-induced rotational components housed in the instrument which cause the wheel to be propelled along the surface with which it is in contact, or by friction-induced sympathetic rotation caused by advancing a freely mounted wheel while in engaged contact with the organ surface. The wheel is rolled along a measurement path, and rotation thereof sensed and converted into data output representative of a distance traversed by the wheel. In a preferred embodiment, the radial positioning of the wheel relative the barrel portion is user selectable, facilitating its use in directionally restricted internal regions. A hood is advantageously provided at the distal end of the barrel portion for covering approximately one half of the peripheral contact arc of the wheel, thereby prevent interference with opposed organ surfaces while a measurement is being taken.

20 Claims, 3 Drawing Sheets

LAPAROSCOPIC INSTRUMENT

BACKGROUND OF THE INVENTION

The present invention relates to a laparoscopic instrument and, more particularly, to a laparoscopic instrument which may be used to determine the values of various internal distances and/or dimensions within a body cavity in connection with laparoscopic surgery.

During laparoscopic surgery, various surgical instruments are inserted through one or more tiny incisions in a patient's abdomen. A example of such a device is disclosed in U.S. Pat. No. 5,147,373 issued Sep. 15, 1992 to Ferzli, which patent is incorporated herein by reference as it pertains to the general construction of such instruments as well as any other structural features pertinent to the practice of the invention herein. In conjunction with the use of laparoscopic devices, a TV monitor receiving electronically converted images from an endoscope displays a view of the interior body cavity being operated on, permitting the surgeon to properly manipulate the laparoscopic instruments to achieve the desired corrective results.

With the advent of laparoscopic surgery many surgical procedures previously requiring major surgery may now be performed with minimal invasion, resulting in a reduction in pain, accelerated patient recovery and significantly less scaring. However, insofar as the only view the surgeon generally has of the interior regions accessed by the laparoscopic instruments is that shown on a monitor, it is often difficult to ascertain distances and dimensions of the various organs or lesions to subject of a particular procedure or operation. Precise measurement of these dimensions and distances could prove quite useful, particularly for example in operations requiring organ bypass, such as in connection with intestinal surgery, where a length of an intestine is ideally bypassed with a correctly sized segment. Also, the size of a tumor or lesion may be determined in situ, such that the extent of the surgery, and the nature and positioning of the required incisions and subsequent suturing, can be better planned in advance of removal.

It would therefore be desirable to provide an instrument for use during laparoscopic surgery which could be inserted into a body cavity through a laparoscopic incision, and which could be used to indicate to the surgeon various internal distances and dimensions.

SUMMARY OF THE INVENTION

Accordingly, it is an object of the invention to provide a laparoscopic instrument which overcomes the drawbacks of the prior art.

It is a further object of the invention to provide a laparoscopic instrument, which when used during a laparoscopic procedure permits physical measurement of various surface distances along internal body masses within a body cavity, for example the size of a duct, vessel, graft or a prothesis.

It is a still further object of the invention to provide a laparoscopic instrument which is relatively simple to operate, and of suitable dimension to permit insertion into a body cavity in a manner compatible with other laparoscopic devices used in conjunction therewith for minimally invasive surgery.

It yet a further object of the invention which structurally lends itself to material fabrication in a form permitting sterilization of the instrument in an autoclave or by means of other accepted sterilization techniques.

It is yet a further object of the invention to provide a laparoscopic instrument which provides versatile measurement capabilities permitting its use independent of internal spacial considerations.

In accordance with these and other objects of the invention, there is provided a laparoscopic instrument which, in broad terms, includes a wheel rotatably mounted at a distal end of an elongated barrel portion. The wheel is of suitable configuration and composition to be biologically inert with respect to internal organs and body chemistry in general, and which, along with the remaining structural components of the instrument is autoclavable prior to and after use. The wheel is placed in contact with the internal body part to be measured and rotation imparted to the wheel, either by self-induced rotational means housed in the instrument which cause the wheel to be propelled along the surface with which it is in contact, or by friction-induced sympathetic rotation caused by advancing a freely mounted wheel while same is in contact with the organ surface. The wheel is thus rolled along a measurement path, the barrel portion being appropriately manipulated in correspondence to a direction of wheel travel. Means are provided for sensing and converting rotation of the wheel into data representative of a distance traversed over an internal body surface by the wheel in contact therewith.

According to a feature of the invention, there is further provided a laparoscopic instrument as mentioned broadly above, in which the elongated barrel portion is advantageously of rigid construction. Mounting of the measurement wheel is accomplished by means permitting user-selectable angular orientation of a rotational axis thereof with respect to the barrel portion. As such the instrument is not limited to rotation along a particular path direction determined by a fixed mounting position of the wheel, making its use in confined spaces or directionally restricted regions more versatile.

According to a still further feature of the invention, there is further provided a laparoscopic instrument in which a hood, covering approximately one half of the peripheral contact arc of the wheel, is fashioned at the distal end of the barrel portion. This feature operates to prevent interference with opposed organ surfaces while a measurement is being taken, which frictional drag attendant therewith might otherwise impede accurate representational rotation of the measurement wheel relative the measurement path.

In an advantageous embodiment, a laparoscopic instrument in accordance with the invention includes the basic configuration of the above embodiments, further means for imparting motor rotation to the measurement wheel such that it may be self propelled along a contact surface to be measured, and which means are mountable at a proximal end of the elongated barrel portion of the instrument to permit selective removal of same for partial autoclaving of only the insertion portion of the measurement instrument or disposal and replacement of same.

In yet another embodiment in accordance with the invention, a length portion of the elongated barrel portion of a laparoscopic instrument for distance measurement adjacent the distal end thereof is flexible to permit the wheel, mounted at the end of the barred portion, to reach locations within a body cavity otherwise inaccessible by an instrument presenting rigidly structured straight barrel configuration. Bending of the flexible portion may be accomplished passively, by virtue of yeildably following a bounded path within the body, such as when the device is inserted to follow an intral segment of an intestinal tract, or alternatively, bending may be user controlled by means putting selective bending from exterior the body cavity, for example by a control at the proximal end of the laparoscopic instrument.

In accordance with yet another feature of the invention, data output from the laparoscopic instrument representative of a distance traversed by the measurement wheel is converted into a form suitable for numerical display in desired units of measurement on a T.V. monitor, for example as an insert or subtitle appearing on the same screen on which is displayed an interior view of the body cavity received by the endoscope, and which displayed image guides the surgeon.

Yet another embodiment of the invention provides the above features in a form in which all or part of the laparoscopic instrument is disposable, thereby permitting cost effective manufacture of same by bio-compatible components and materials which would not otherwise be repeatedly autoclavable.

The above, and other objects, features and advantages of the present invention will become apparent from the following description read in conjunction with the accompanying drawings, in which me reference numerals designate the same elements.

DETAILED DESCRIPTION OF THE INVENTION

Figure 1:
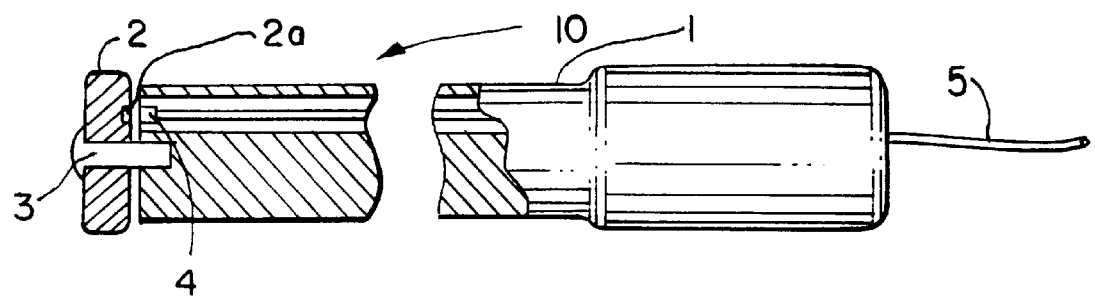
FIG. 1 is a simplified side elevation shown in partial cross-section of a laparoscopic instrument in accordance with an embodiment of the invention, and in which a measurement wheel is mounted with an axis of rotation thereof codirectional with a longitudinal axis of a barrel portion of the instrument.

Referring to FIG. 1, there is shown a laparoscopic instrument in accordance with an embodiment of the invention, generally designated 10. Laparoscopic instrument 10 includes a barrel portion 1 of elongated configuration and narrow cross-section to be compatible with insertion into a body cavity through a laparoscopic incision made in the abdominal wall. A wheel 2 is rotationally mounted at a distal end of barrel portion 1, in the depicted embodiment, freely mounted for low-frictional rotation about a bearing 3, enabling wheel 2 to rotate as a consequence of frictionally applied rotational forces created by advancement thereof along a surface which it is in frictional contact. In the embodiment of FIG. 1, wheel 2 is oriented with an axis of rotation codirectional with a longitudinal axis of barrel portion 1. Such positioning is primarily suited to measurement across an organ, a travel path of wheel 2 roughly defined by a broad circular arc having an origin at the point of insertion through the laparoscopic incision. Means are provided for sensing and converting rotation of wheel 2 into data representative of a distance traversed over an internal body surface by the when in contact therewith, conveniently provided in the form of a plurality of radially disposed markers 2a and a sensor 4 for detecting and producing a pulsed output or other measurable circuit quantity in response to movement of markers 2a past sensor 4. A cable 5 exiting laparoscopic instrument 10, optionally detachable from a remainder of laparoscopic instrument 10, is provided to communicate signals received from sensor 4 to a remote processor for converting the pulsed output into a numerical representation of linear distance traversed by wheel 2, such calculated figure being a function of wheel circumference and number of radially disposed markers 2a per wheel 2. The nature of markers 2a will depend upon the functionality of sensor 4. For example, where sensor 2a is an induction type device, markers 2a are comprised of a material effecting magnetic fields. When instead, sensor 4 includes optically induced means for detection, markers 2a may be comprised of a material which differs in reflectivity from a material surface presented on wheel 2 between markers 2a, either being more or less reflective.

Figure 2:
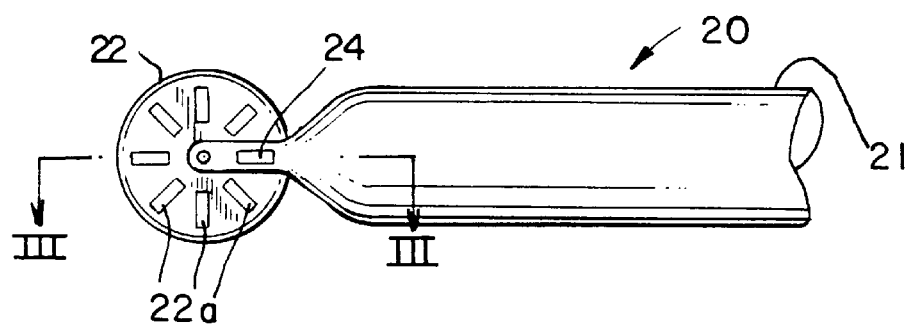
FIG. 2 is a simplified side elevation shown in partial cross-section of a laparoscopic instrument in accordance with another embodiment of the invention, and in which a measurement wheel is mounted with an axis of rotation thereof perpendicular with a longitudinal axis of a barrel portion of the instrument.
Figure 3:
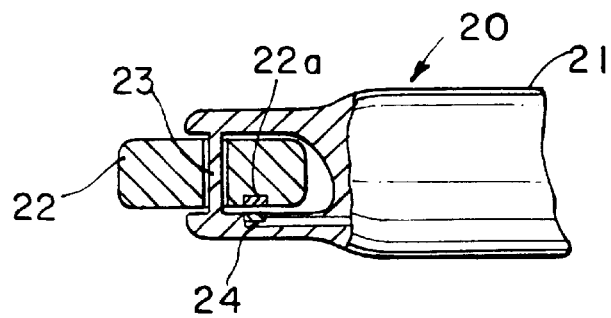
FIG. 3 is cross-sectional plan view taken on lines III—III of FIG. 2.

Turning now to FIGS. 2 and 3, an alternative embodiment of a laparoscopic instrument is depicted, directed to measurement along a path codirectional with a direction of instrument insertion, generally designated 20. Laparoscopic instrument 20, is analogously configured with laparoscopic instrument 10 of FIG. 1, and includes an elongated barrel portion 21 and a wheel 22 mounted about a bearing 23 at a distal end thereof. As in the previous embodiment, wheel 22 includes a plurality of radially displaced markers 22a and a sensor 24 which includes means for detecting movement of same past sensor 24 as wheel 22 rotates.

The above described embodiments are dedicated to measurement along predefined paths, and as such are limited in scope as to particular applications. In this regard, various embodiments are contemplated and which are directed to a laparoscopic instrument design which enables a user to select, either prior to insertion into a body cavity, or continuously during active use, angular orientation of a rotational axis of the distally mounted measurement wheel with respect to the barrel portion. As such, the instrument is not limited to rotation along a particular path direction determined by a fixed mounting position of the wheel, making its use in confined spaces or directionally restricted regions more versatile.

Figure 4:
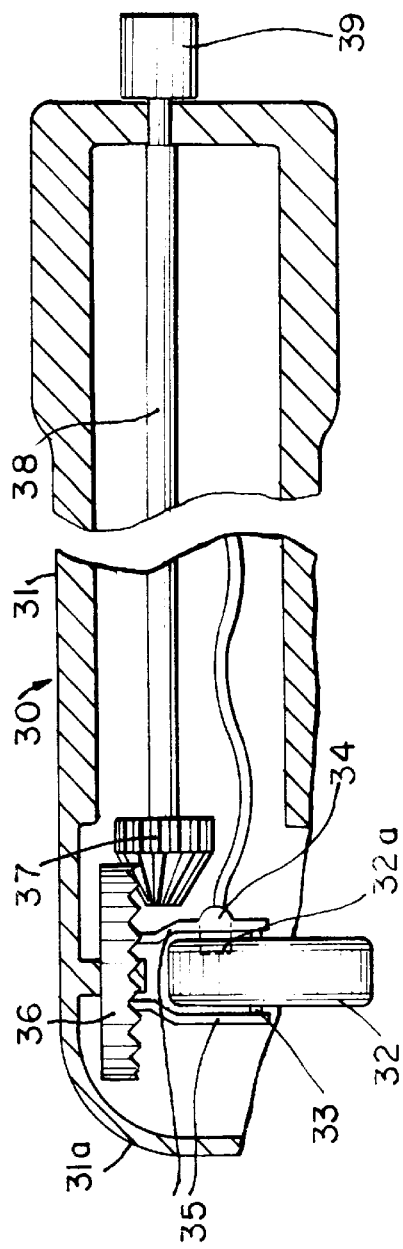
FIG. 4 is an elevational view shown in partial cross-section of another embodiment in accordance with the invention, and which provides means for rotationally positioning the rotational axis of the measurement when.
Figure 5:
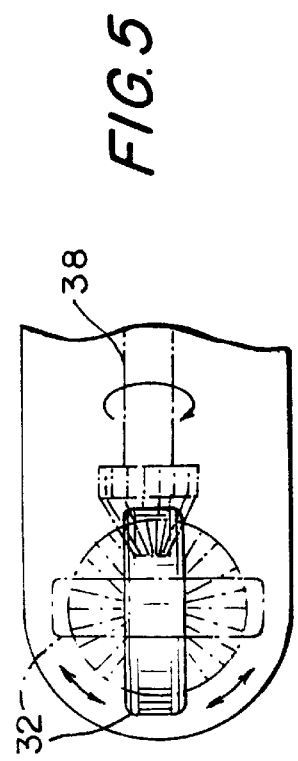
FIG. 5 is a schematic operational view shown in plan of the embodiment of FIG. 4.

Referring now to FIG. 4, a laparoscopic instrument, generally designated 30, is directed to an example of a device which includes means for continuous user-selection of angular wheel position. A wheel 32 is mounted at a distal end of a barrel portion 31. Wheel 32 is rotatably supported on an axle 33 extending between a pair of lateral supports 35. Lateral supports 35 are fixed to a bevel gear 36 which in turn is supported by and rotatable with respect to barrel portion 31. A rotatable shaft 38 extends the length of barrel portion 31. A bevel gear is disposed on a distally located terminal end of shaft 31 which cooperatingly engages bevel gear 36, and an adjustment knob 39 is carried on the proximally located end thereof. Rotation of adjustment knob 39 effects rotation of bevel gear 36 enabling selective angular orientation of wheel 32 attached thereto, as shown in the operation view depicted in FIG. 5, the arrows indicating relative motion of shaft 38 and wheel 32.

In taking into account the particular environmental constraints attendant internal surgery, a laparoscopic instrument in accordance with various embodiments of the invention within the contemplated scope as claimed herein advantageously includes structure preventing interference with opposed organ surfaces while a measurement is being taken, which frictional drag caused thereby might otherwise impede accurate representational rotation of the measurement wheel relative the measurement path. As shown in FIG. 4, a hooded portion 31 is provided at the distal end of barrel portion 31, hooded portion 31 conveniently being a continuation of structure comprising barrel portion 31, and covering approximately one half of the peripheral contact arc of wheel 32.

In the aforementioned embodiments, rotation is sympathetically imparted to the freely mounted measurement wheel by advancement thereof while in frictional contact with the body part to be measured. In the alternative, if so desired, self-induced means for rotating the wheel may be provided, for example, conveniently in the form of an energizable servo-motor, which causes the measurement to be selectively propelled in a given measurement directing.

Figure 6:
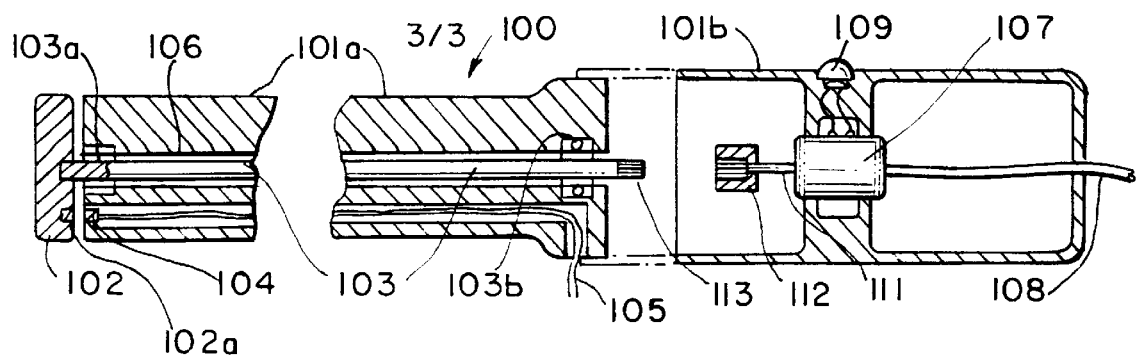
FIG. 6 is a simplified side elevation shown in partial cross-section of a laparoscopic instrument in accordance with an embodiment of the invention in which a motor driven measurement wheel is mounted with an axis of rotation thereof codirectional with a longitudinal axis of a barrel portion of the instrument.

Turning now to FIG. 6, an embodiment of a laparoscopic instrument in which such feature is provided is depicted, in which the laparoscopic instrument is generally designated 100. Laparoscopic instrument 100 includes a forward portion 100a and a handle portion 100b receivable in mounted engagement therewith, as will be described in greater detail hereinafter. Forward portion 100a is of the same general construction of the embodiment described above with respect to FIG. 1, and includes a distally mounted measurement wheel 102 including one or more markers 102a, and a sensor 104 for detecting movement of markers 102a therepast. Instead, however, of being freely mounted for rotation about a bearing, measurement wheel 102 is fixed to a rotatable spindle 103 running the length of elongated forward portion 10a, internal of a spindle bore 106 in which it is received in clearance fit. Means for insuring reliable, reduced-friction rotatability of spindle 103 is advantageously provided, conveniently in the form of a forward being 103a and a rearward bearing 103b which keeps spindle 103 isolated from interior walls of spindle bore 106. A servo motor 107 is mounted in handle portion 100b, and receives power, advantageously of low voltage and current, from an external source through a power cord 108. Servo motor 107 is selectively energized by depression of an outwardly biased external activation button 109. Servo motor 107 includes a sht 111, a distal end of which carries a drive transmission coupling 112. A drive receiving coupling 113 is carried on a proximal end of spindle 103, and is adapted to engage drive transmission coupling 112 when handle portion 110b is mountably engaged with forward portion 100a, as shown in phantom. Rather than simple interference fit, as shown for purposes of simplifying illustration, such mounted engagement may be advantageously accomplished by cooperating bayonet mounting structure carried on both forward portion 100a and handle portion 100b. By providing laparoscopic instrument 100 in separable portions, as described above, a portion thereof, i.e. forward portion 100a, can be made to be disposable, and the remaining portion containing more costly components can be designed to be autoclavable, for sterilization between use.

Figure 7:
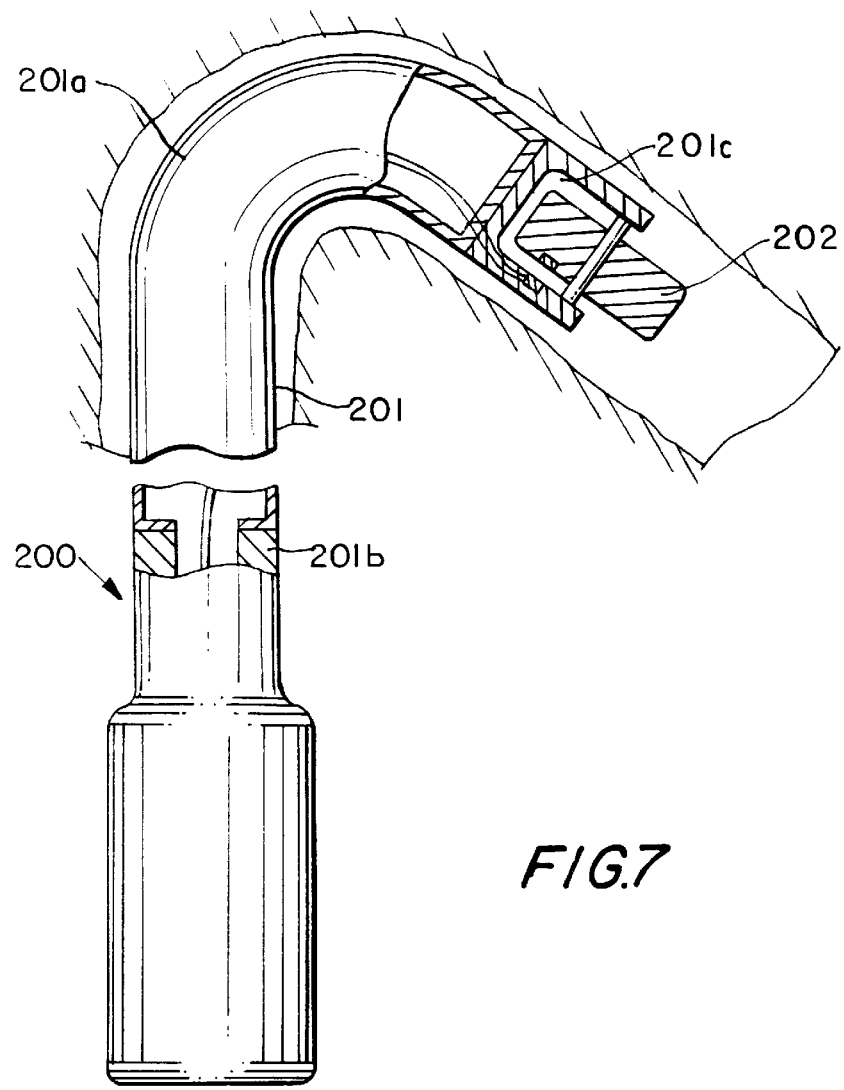
FIG. 7 is a simplified plan view in partial cross-section of a laparoscopic instrument in accordance with another embodiment of the invention which includes a flexible elongated barrel portion.

Turning now to FIG. 7, another embodiment of a laparoscopic instrument in accordance with the invention is depicted, generally designated 200, and which provides the required versatility where curves must be negotiated within confined spaces. Laparoscopic instrument 200 in the depicted example is, for purposes of illustration, constructed in general conformance with that of the embodiment described with regard to FIG. 2, and includes an elongated barrel portion 201 of cross-sectional dimension compatible with insertion onto a laparoscopic incision. In variance, however, with the previously described embodiment, elongate barrel portion 201 is of material and construction which permits flexing thereof over a length portion 201a, advantageously positioned adjacent a distal end thereof. Barrel portion 201 also includes a rigid base portion 201b fixed to flexible portion 201a at its proximal end, and a rigid end portion 201c attached at its distal end. A measurement wheel 202 is rotatably mounted at rigid end portion 201c in a manner analogous to that of laparoscopic instrument 20 of FIG. 2. Bending of the flexible portion may be accomplished passively, by virtue of yeildably following a bounded path within the body, such as when the device is inserted to follow an internal segment of an intestinal tract, as shown. Alternatively, a bendable structure that holds a particular shape when bent prior to insertion into the body cavity, and incorporating known structural configurations and materials to accomplish such function, may be used in the construction of flexible portion 201a. In addition, structure permitting bending to be user controlled by means permitting selective bending from exterior the body cavity, for example by a control at the proximal end of the laparoscopic instrument, may be employed. Structural means for accomplishing such bendable structure is disclosed for example in U.S. Pat. No. 4,292,961 issue on Oct. 6, 1981 to Kawashima, and which is incorporated herein by reference for its teaching regarding the general construction of bendable devices for insertion into a body cavity.

To provide convenience and efficiency to the surgeon guiding the various laparoscopic instruments used during such surgery in taking distance measurements with the derive in accordance with embodiment of the invention, data output from the laparoscopic instrument representative of a distance traversed by the measurement wheel may be converted into a form for numerical display in desired units of measurement on a T.V. monitor, for example as an insert or subtitle on the same monitor on which is displayed an interior view of the body cavity received by the endoscope guiding the surgeon. As such, all data, including visual and numerical, are available in a consolidated location for easy, simultaneous viewing.

It is noted, that with respect to the laparoscopic instrument in accordance with any of the embodiments specifically described herein or within the contemplated scope of the invention, all or part of such instrument may be disposable after use. Such construction obviates the need for sterilization after use, for greater convenience, while concomitantly permitting manufacture of at least parts thereof using more cost efficient bio-compatible materials which would otherwise be prone to wear after regular use or which might not withstand repeated autoclaving.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A laparoscopic instrument for distance measurement of a surface internal of a body, comprising:

an elongated barrel portion presenting structure at a proximal end portion thereof for controlled hand-held grasping;

a wheel rotatably mounted at a distal end of said barrel portion, said wheel being contactable with the surface internal of the body;

a wheel rotation sensor which produces signals in response to a rotation of said wheel;

a convertor which converts the signals representative of the rotation of the wheel produced by said wheel rotation sensor into numerical data representative of a distance traversed over an internal body surface by the wheel while maintained in contact therewith; and a transmission path via which at least one of said signals and said numerical data can be transmitted to a location remote from said elongated barrel portion.

2. A laparoscopic instrument according to claim 1, further comprising at least one marker disposed in a radial position on said wheel, and said wheel rotation sensor including means for detecting passage of said at least one marker therepast and for producing a measurable circuit quantity in response thereto.

3. A laparoscopic instrument according to claim 1, further comprising an angle adjustment mechanism which permits user selection of an angular orientation of a rotational axis of said wheel with respect to a longitudinal axis of said barrel portion.

4. A laparoscopic instrument for distance measurement of a surface internal of a body, comprising:

an elongated barrel portion presenting structure at a proximal end portion thereof for controlled hand-held grasping;

a wheel rotatably mounted at a distal end of said barrel portion, said wheel being contactable with the surface internal of the body; and means for sensing and converting rotation of the wheel into data representative of a distance traversed over an internal body surface by the wheel while maintained in contact therewith;

angle adjustment means for user selecting an angular orientation of a rotational axis of said wheel with respect to a longitudinal axis of said barrel portion, said angle adjustment means being operable from a point at said proximal end portion.

5. A laparoscopic instrument according to claim 1, further comprising a hooded portion disposed at said distal end of said barrel portion, for shielding at least a portion of one half of a peripheral contact arc of said wheel from contact with surrounding structure within the body.

6. A laparoscopic instrument according to claim 5, wherein said hooded portion is a contiguous extension of structure comprising said barrel portion.

7. A method of measuring a surface internal of a body, comprising the steps of:

providing a laparoscopic instrument having an elongated barrel portion and a wheel rotatably mounted on a distal end thereof, said laparoscopic instrument further comprising means for sensing and converting rotation of the wheel into a readout value;

inserting said elongated barrel at least partially into a laparoscopic incision;

contacting the surface internal of the body with said wheel;

moving the wheel while said wheel remains in contact with the surface, whereby said readout value is changed from an initial value prior to rotation of the when by an amount proportional to a distance traveled by the wheel over the surface; and converting said amount into a value representative of the distance traveled by the wheel.

8. A method according to claim 7, further comprising selectively adjusting a desired angular orientation of a rotational axis of the wheel relative to the barrel portion at least one of prior to said step of inserting and following said step of inserting during active use.

9. A method according to claim 7, further comprising displaying said value representative of the distance traveled by the wheel on a monitor.

10. A method according to claim 9, further comprising further displaying, simultaneously with said step of displaying, a view of the surface internal of the body on the monitor employed in said step of displaying.

11. A method according to claim 10, wherein said value representative of the distance traveled by the wheel is shown as at least one of an insert and a superimposed image on the monitor in said steps of displaying and further displaying.

12. A laparoscopic instrument according to claim 1, wherein said transmission path includes a cable exiting said elongated barrel portion.

13. A laparoscopic instrument according to claim 12, wherein said cable is detachable from a remainder of said laparoscopic instrument.

14. A laparoscopic instrument according to claim 1, further comprising a motor for imparting rotation to the wheel.

15. A laparoscopic instrument according to claim 14, wherein said motor is drivably coupled to the wheel in a manner permitting selective removal of said motor from a remainder of the laparascopic instrument.

16. A laparoscopic instrument according to claim 1, wherein the laparoscopic instrument is made in detachable sections, at least one of said detachable sections being autoclavable.

17. A laparoscopic instrument according to claim 1, wherein the laparoscopic instrument is made in detachable sections, at least one of said detachable sections being disposable.

18. A laparoscopic instrument for distance measurement of a surface internal of a body, comprising:

an elongated barrel portion presenting structure at a proximal end portion thereof for controlled hand-held grasping, at least a length portion of said elongated barrel portion being at least one of flexible and bendable;

a wheel rotatably mounted at a distal end of said barrel portion, said wheel being contactable with the surface internal of the body;

a wheel rotation sensor which produces signals in response to a rotation of said wheel; and a convertor which converts the signals representative of the rotation of the wheel produced by said wheel rotation sensor into numerical data representative of a distance traversed over an internal body surface by the wheel while maintained in contact therewith.

19. A laparoscopic instrument according to claim 18, wherein said at least a length portion being located adjacent the distal end of said elongated barrel portion.

20. A method of measuring a surface internal of a body, comprising the steps of:

provided a laparoscopic instrument having an elongated barrel portion and a wheel rotatably mounted to said elongated barrel;

inserting said elongated barrel at least partially into a laparoscopic incision;

contacting the surface internal of the body with said wheel;

moving the wheel an incremental distance along the surface while said wheel remains in contact with the surface;

sensing an amount of rotation of said wheel during said step of moving; and converting the amount of rotation into a value representative of the incremental distance.

* * * * *